United States Patent
Kutikov et al.

(10) Patent No.: US 9,320,736 B2
(45) Date of Patent: Apr. 26, 2016

(54) ZINC CHELATING AGENTS FOR DEPLETING XIAP AND SENSITIZING TUMOR CELLS TO APOPTOSIS

(71) Applicant: Institute for Cancer Research, Philadelphia, PA (US)

(72) Inventors: Alexander Kutikov, Voorhees, NJ (US); Vladimir Kolenko, Philadelphia, PA (US); Seth M. Cohen, San Marcos, CA (US); Robert G. Uzzo, Ambler, PA (US); Ervin Teper, Huntington Valley, PA (US)

( * ) Notice: Subject to any disclaimer, the term of this patent is extended or adjusted under 35 U.S.C. 154(b) by 0 days.

(21) Appl. No.: 14/610,044

(22) Filed: Jan. 30, 2015

(65) Prior Publication Data
US 2015/0147291 A1     May 28, 2015

Related U.S. Application Data

(63) Continuation of application No. PCT/US2013/052495, filed on Jul. 29, 2013.

(60) Provisional application No. 61/677,202, filed on Jul. 30, 2012.

(51) Int. Cl.
| | |
|---|---|
| *A61K 31/47* | (2006.01) |
| *A61K 38/19* | (2006.01) |
| *A61K 45/06* | (2006.01) |
| *A61K 31/4709* | (2006.01) |

(52) U.S. Cl.
CPC .............. *A61K 31/47* (2013.01); *A61K 31/4709* (2013.01); *A61K 38/191* (2013.01); *A61K 45/06* (2013.01)

(58) Field of Classification Search
CPC .............................. A61K 31/47; A61K 38/191
See application file for complete search history.

(56) References Cited

U.S. PATENT DOCUMENTS

| | | |
|---|---|---|
| 2008/0207673 A1 | 8/2008 | Xilinas |
| 2010/0041653 A1 | 2/2010 | Pellecchia et al. |

FOREIGN PATENT DOCUMENTS

WO    WO 2012122534 A2 *  9/2012

OTHER PUBLICATIONS

Rouffet et al. J. Am. Chem. Soc. 2010, vol. 132, pp. 8232-8233.*
Makhov, P., et al., "Zinc chelation induces rapid depletion of the X-linked inhibitor of apoptosis (XIAP) and sensitizes prostate cancer cells to TRAIL-mediated apoptosis", Cell Death Differ., Nov. 2008; 15(11):1745-1751.
Fahrni, C., et al., "Aqueous Coordination Chemistry of Quinoline-Based Fluorescence Probes for the Biological Chemistry of Zinc", J. Am. Chem. Soc., 1999, 121:11448-11458.
Kolenko, V., et al., "Inhibition of NF-kB Activity in Human T Lymphocytes Induces Caspace-Dependent Apoptosis without Detectable Activation of Caspase-1 and -3(1)", J. Immunol., 1999, 163:590-598.
Schimmer, A., et al., "Targeting XIAP for the treatment of malignancy", Cell Death Differ., 2006, 13:179-188.
Cheung, H.H., et al., "X-Linked Inhibitor of Apoptosis Antagonism: Strategies in Cancer Treatment", Clin. Cancer Res., 2006; 12(11):3238-3242.
Schimmer, A., et al., "Small-molecule antagosists of apoptosis suppressor XIAP exhibit broad antitumor activity", Cancer Cell, Jan. 2004; 5(1):25-35. (Abstract Only).
International Search Report and Written Opinion issued Dec. 6, 2013 in related international application PCT/US2013/052495.

* cited by examiner

*Primary Examiner* — James D Anderson
(74) *Attorney, Agent, or Firm* — Stradley Ronon Stevens & Young, LLP

(57) ABSTRACT

The invention provides zinc chelating agents and formulations thereof that deplete XIAP in cancer cells and sensitize the cells to apoptosis-inducing agents. The invention provides methods for sensitizing apoptosis-resistant cancer cells to apoptosis-inducing agents, as well as methods for treating a subject with a combined therapy of a zinc chelating agent and an apoptosis-inducing agent.

18 Claims, 2 Drawing Sheets

Level of measured apoptosis in castration-resistant (PC-3) prostate cancer cells

| CONDITIONS | % APOPTOSIS | |
|---|---|---|
| PC3 Cloning Medium | 1.94 | |
| PC3 + TRAIL | 5.20 | |
| CHELATOR | Chelator Only | TRAIL + Chelator |
| MR 13 | 10.48 | 80 |
| MR 44 | 4.47 | 67.95 |
| CHELATOR (CONTROL) | | |
| MR 66 | 0.55 | 4.05 |
| MR 96 | 5.33 | 1.12 |

ZINC CHELATING AGENTS FOR DEPLETING XIAP AND SENSITIZING TUMOR CELLS TO APOPTOSIS

CROSS REFERENCE TO RELATED APPLICATIONS

This application is a continuation of International Application No. PCT/US2013/052495, filed on Jul. 29, 2013, and claims priority to U.S. Provisional Application No. 61/677,202, filed on Jul. 30, 2012, the contents of each application are incorporated by reference herein, in their entirety and for all purposes.

STATEMENT OF GOVERNMENT SUPPORT

The inventions described herein were made, in part, with funds obtained from the National Institutes of Health, Grant Nos. R01-CA108890 and R01-CA134463, and from the U.S. Department of Defense, Grant No. W81XWH-10-1-018. The U.S. government may have certain rights in these inventions.

FIELD OF THE INVENTION

The invention relates generally to the field of cancer treatment. More particularly, the invention relates to combination therapies for treating cancer cells, and especially for enhancing the susceptibility of cancer cells to cytotoxic agents by depleting proteins that support resistance to cell death.

BACKGROUND OF THE INVENTION

Various publications, including patents, published applications, technical articles and scholarly articles are cited throughout the specification. Each of these cited publications is incorporated by reference herein, in its entirety and for all purposes.

Castration-resistant prostate cancer (CRPC) is the second leading cause of cancer death among men in the United States. Current treatment options, including docetaxel-based chemotherapy and more recently Sipuleucel-T, have been shown to improve survival by only 2 to 4 months. Furthermore, androgen ablation—a mainstay treatment for advanced prostate cancer—is coming under increasing scrutiny due to the well-documented reduction in the quality of life, unclear impact on survival, and increasingly better understood ill-effects on cardiovascular health. Development of new therapeutic strategies for advanced prostate cancer represents an urgent need in today's clinical landscape.

SUMMARY OF THE INVENTION

The invention provides compounds of Formula I

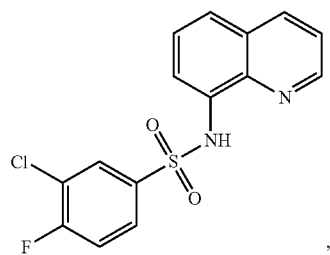

(I)

or a pharmaceutically acceptable salt thereof. As well, the compound may be comprised in a composition with a pharmaceutically acceptable carrier.

The invention also provides compounds of Formula II

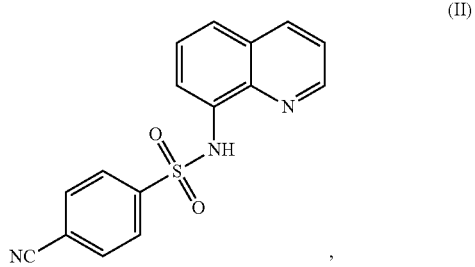

(II)

or a pharmaceutically acceptable salt thereof. As well, the compound may be comprised in a composition with a pharmaceutically acceptable carrier.

The invention also provides compounds of Formula V

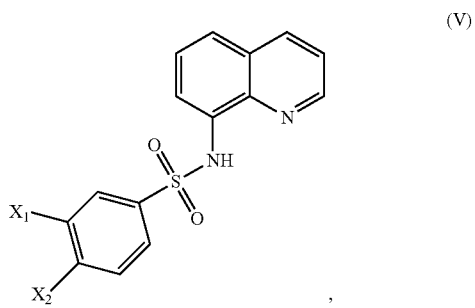

(V)

or a pharmaceutically acceptable salt thereof, wherein X1 is H, Cl, or F; and X2 is CN, or F. In some preferred aspects of formula V, X1 is Cl and X2 is F. In some preferred aspect of Formula V, X1 is H and X2 is CN. As well, the compound may be comprised in a composition with a pharmaceutically acceptable carrier.

The compounds of Formula I, Formula II, and/or Formula V, the respective pharmaceutically acceptable salts thereof, and compositions comprising these compounds or pharmaceutically acceptable salts may be used in various methods. In some aspects, a method comprises depleting X-linked inhibitor of apoptosis protein (XIAP) in a cell, and comprises contacting the cell with an amount of a compound having Formula I or a pharmaceutically acceptable salt thereof, effective to deplete XIAP in the cell. In some aspects, a method comprises depleting XIAP in a cell, and comprises contacting the cell with an amount of a compound having Formula II or a pharmaceutically acceptable salt thereof, effective to deplete XIAP in the cell. In some aspects, a method comprises depleting XIAP in a cell, and comprises contacting the cell with an amount of a compound having Formula V or a pharmaceutically acceptable salt thereof, effective to deplete XIAP in the cell. The compound of Formula I or Formula II or Formula V may be comprised in a composition with a pharmaceutically acceptable carrier. The cell is preferably a tumor cell, including a cell of a tumor of the prostate gland. The tumor of the prostate gland may be castration resistant. The XIAP is preferably depleted by about 90% to about 99%, relative to the level of a cell of the same type that has not been contacted with Formula I, Formula II, a respective pharmaceutical salt thereof, or a composition thereof. XIAP depletion preferably comprises degradation of XIAP protein.

In some aspects, a method comprises chelating zinc in a cell, and comprises contacting the cell with an amount of a compound having Formula I, or a pharmaceutically acceptable salt thereof, effective to chelate zinc in the cell. In some aspects, a method comprises chelating zinc in a cell, and comprises contacting the cell with an amount of a compound having Formula II, or a pharmaceutically acceptable salt thereof, effective to chelate zinc in the cell. In some aspects, a method comprises chelating zinc in a cell, and comprises contacting the cell with an amount of a compound having Formula V, or a pharmaceutically acceptable salt thereof, effective to chelate zinc in the cell. The compound of Formula I or Formula II or Formula V may be comprised in a composition with a pharmaceutically acceptable carrier. The cell is preferably a tumor cell, including a cell of a tumor of the prostate gland. The tumor of the prostate gland may be castration resistant.

In some aspects, a method comprises enhancing the sensitivity of a tumor cell to an apoptosis-inducing agent, and comprises depleting XIAP in the tumor cell to a level at which the cell is sensitive to the apoptosis-inducing agent, and the step of depleting XIAP comprises contacting the cell with an amount of a compound having Formula I, or a pharmaceutically acceptable salt thereof, effective to deplete XIAP in the cell to the level at which the cell is sensitive to the apoptosis-inducing agent. In some aspects, a method comprises enhancing the sensitivity of a tumor cell to an apoptosis-inducing agent, and comprises depleting XIAP in the tumor cell to a level at which the cell is sensitive to the apoptosis-inducing agent, and the step of depleting XIAP comprises contacting the cell with an amount of a compound having Formula II, or a pharmaceutically acceptable salt thereof, effective to deplete XIAP in the cell to the level at which the cell is sensitive to the apoptosis-inducing agent. In some aspects, a method comprises enhancing the sensitivity of a tumor cell to an apoptosis-inducing agent, and comprises depleting XIAP in the tumor cell to a level at which the cell is sensitive to the apoptosis-inducing agent, and the step of depleting XIAP comprises contacting the cell with an amount of a compound having Formula V, or a pharmaceutically acceptable salt thereof, effective to deplete XIAP in the cell to the level at which the cell is sensitive to the apoptosis-inducing agent. The compound of Formula I or Formula II or Formula V may be comprised in a composition with a pharmaceutically acceptable carrier. The tumor cell is preferably a cell of a tumor of the prostate gland. The tumor of the prostate gland may be castration resistant. The tumor cell may be resistant to the apoptosis-inducing agent in the absence of XIAP depletion. The apoptosis-inducing agent may comprise TRAIL, or an apoptosis-inducing derivative thereof. XIAP depletion preferably comprises degradation of XIAP protein.

In some aspects, a method comprises inducing apoptosis in an apoptosis-resistant cell, and comprises contacting the cell with an amount of a compound having Formula I, or a pharmaceutically acceptable salt thereof, effective to deplete XIAP in the cell, and contacting the cell with an amount of an apoptosis-inducing agent effective to induce apoptosis in the cell. In some aspects, a method comprises inducing apoptosis in an apoptosis-resistant cell, and comprises contacting the cell with an amount of a compound having Formula II, or a pharmaceutically acceptable salt thereof, effective to deplete XIAP in the cell, and contacting the cell with an amount of an apoptosis-inducing agent effective to induce apoptosis in the cell. In some aspects, a method comprises inducing apoptosis in an apoptosis-resistant cell, and comprises contacting the cell with an amount of a compound having Formula V, or a pharmaceutically acceptable salt thereof, effective to deplete XIAP in the cell, and contacting the cell with an amount of an apoptosis-inducing agent effective to induce apoptosis in the cell. The apoptosis-resistant cell is preferably resistant to the apoptosis-inducing agent, and the agent preferably comprises TRAIL or an apoptosis-inducing derivative thereof. The compound of Formula I or Formula II or Formula V may be comprised in a composition with a pharmaceutically acceptable carrier. The apoptosis-resistant cell is preferably a tumor cell of a tumor of the prostate gland. The tumor of the prostate gland may be castration resistant. The tumor cell may be resistant to the apoptosis-inducing agent in the absence of XIAP depletion. The XIAP is preferably depleted by about 90% to about 99%, relative to the level of a cell of the same type that has not been contacted with Formula I, Formula II, or Formula V, a respective pharmaceutical salt thereof, or a composition thereof. XIAP depletion preferably comprises degradation of XIAP protein.

The invention also features methods for treating an apoptosis-resistant tumor in a subject in need thereof. In some aspects, the methods comprise administering to the subject an amount of a compound having Formula I, or a pharmaceutically acceptable salt thereof, effective to deplete XIAP in cells of the tumor, and administering to the subject an amount of an apoptosis-inducing agent effective to induce apoptosis in cells of the tumor in which XIAP has been depleted. In some aspects, the methods comprise administering to the subject an amount of a compound having Formula II, or a pharmaceutically acceptable salt thereof, effective to deplete XIAP in cells of the tumor, and administering to the subject an amount of an apoptosis-inducing agent effective to induce apoptosis in cells of the tumor in which XIAP has been depleted. In some aspects, the methods comprise administering to the subject an amount of a compound having Formula V, or a pharmaceutically acceptable salt thereof, effective to deplete XIAP in cells of the tumor, and administering to the subject an amount of an apoptosis-inducing agent effective to induce apoptosis in cells of the tumor in which XIAP has been depleted. The compound of Formula I or Formula II or Formula V may be comprised in a composition with a pharmaceutically acceptable carrier. The tumor is preferably a tumor of the prostate gland, which may be castration resistant. The XIAP is preferably depleted by about 90% to about 99% in cells of the tumor. The apoptosis-inducing agent may comprise TRAIL, or an apoptosis-inducing derivative thereof. The subject is preferably a human being. XIAP depletion preferably comprises degradation of XIAP protein.

The invention also features kits. The kits may be used to practice any of the methods described or exemplified herein. In some aspects, the kits comprise a compound having Formula I, or a pharmaceutically acceptable salt thereof, in an amount effective to deplete XIAP in a cell, an amount of TRAIL or an apoptosis-inducing derivative thereof effective to induce apoptosis in a XIAP-depleted cell, and instructions for using the compound or pharmaceutically acceptable salt thereof and the TRAIL or apoptosis-inducing derivative thereof in the method, for example, a method for enhancing the sensitivity of a tumor cell to an apoptosis-inducing agent, for example, TRAIL, or a method for inducing apoptosis in an apoptosis-resistant cell, or a method for treating an apoptosis-resistant tumor in a subject in need thereof. In some aspects, the kits comprise a compound having Formula II, or a pharmaceutically acceptable salt thereof, in an amount effective to deplete XIAP in a cell, an amount of TRAIL or an apoptosis-inducing derivative thereof effective to induce apoptosis in a XIAP-depleted cell, and instructions for using the compound or pharmaceutically acceptable salt thereof and the TRAIL or apoptosis-inducing derivative thereof in the method, for example, a method for enhancing the sensitivity of a tumor cell to an apoptosis-inducing agent, for example, TRAIL, or a method for inducing apoptosis in an apoptosis-resistant cell, or a method for treating an apoptosis-resistant tumor in a subject in need thereof. In some aspects, the kits comprise a compound having Formula V, or a pharmaceutically acceptable salt thereof, in an amount effective to deplete XIAP in a cell, an amount of TRAIL or an apoptosis-inducing derivative thereof effective to induce apoptosis in a XIAP-depleted cell, and instructions for using the compound or pharmaceutically acceptable salt thereof and the TRAIL or apoptosis-inducing derivative thereof in the method, for example, a method for enhancing the sensitivity of a tumor cell to an apoptosis-inducing agent, for example, TRAIL, or a method for inducing apoptosis in an apoptosis-resistant cell, or a method for treating an apoptosis-resistant tumor in a subject in need thereof. The kit may comprise a pharmaceutically acceptable carrier into which the compound of Formula I or Formula II or Formula V, and/or the TRAIL or an apoptosis-inducing derivative thereof may be mixed.

DETAILED DESCRIPTION OF THE INVENTION

Figure 1:
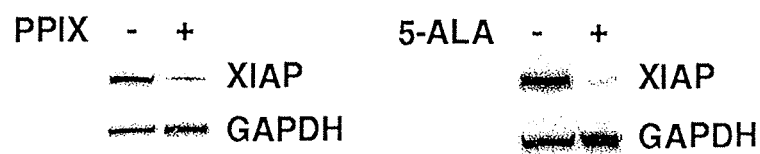
FIG. 1 shows treatment with protoporphyrin IX (PPIX) or 5-Ala reduces XIAP levels in prostate cancer cells. PC-3 cells were cultured in medium alone, or in the presence of PPIX (50 µM) for 4 hours, or 5-Ala (250 µM) for 24 hours. Expression of XIAP and GAPDH (control) was detected by immunoblotting with an antibody to XIAP or GADPH, respectively.

Various terms relating to aspects of the present invention are used throughout the specification and claims. Such terms are to be given their ordinary meaning in the art, unless otherwise indicated. Other specifically defined terms are to be construed in a manner consistent with the definition provided herein.

As used herein, the singular forms "a," "an," and "the" include plural referents unless expressly stated otherwise.

The term "about" as used herein encompasses variations of plus or minus 25%, 20%, 15%, 10%, 5%, 1%, 0.5%, 0.25%, or 0.1% from the specified value.

The terms subject and patient are used interchangeably herein. A subject may be any animal, including a mammal such as a farm animal (e.g., horse, cow, sheep, pig), laboratory animal (e.g., mouse, rat, rabbit), companion animal (e.g., dog, cat), or non-human primates (e.g., new world monkey and old world monkey). In highly preferred aspects, the subject is a human being.

MR13 comprises a compound having Formula I, and all pharmaceutically acceptable salts thereof. Formula I:

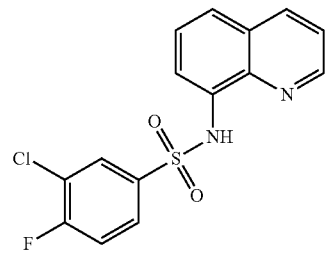

MR44 comprises a compound having Formula II, and all pharmaceutically acceptable salts thereof. Formula II:

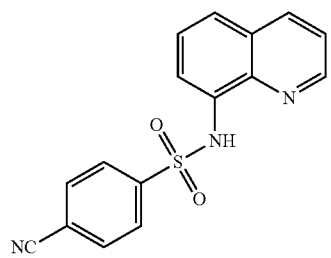

MR66 comprises a compound having Formula III, and all pharmaceutically acceptable salts thereof. Formula III:

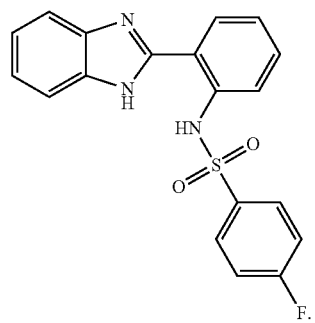 [SMILES: O=S(=O)(Nc1ccccc1-c1nc2ccccc2[nH]1)c1ccc(F)cc1]

MR96 comprises a compound having Formula IV, and all pharmaceutically acceptable salts thereof. Formula IV:

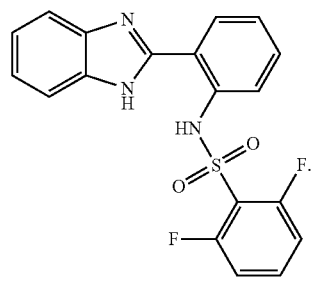 [SMILES: O=S(=O)(Nc1ccccc1-c1nc2ccccc2[nH]1)c1c(F)cccc1F]

Formula V comprises a compound having Formula V, and all pharmaceutically acceptable salts thereof. Formula V:

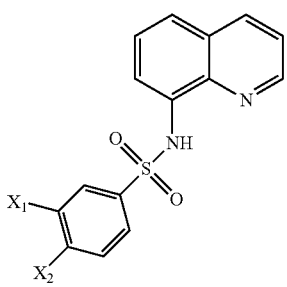

wherein X1 is H, Cl, or F; and X2 is CN, or F. In some preferred aspects of formula V, X1 is Cl and X2 is F. In some preferred aspect of Formula V, X1 is H and X2 is CN.

Pharmaceutically acceptable salts of Formula I, Formula II, and Formula V may be acid or base salts. Non-limiting examples of pharmaceutically acceptable salts include sulfates, methosulfates, methanesulfates, pyrosulfates, bisulfates, sulfites, bisulfites, nitrates, besylates, phosphates, monohydrogenphosphates, dihydrogenphosphates, metaphosphates, pyrophosphates, chlorides, bromides, iodides, fluorides, acetates, propionates, decanoates, caprylates, acrylates, formates, isobutyrates, caproates, heptanoates, propiolates, oxalates, malonates, succinates, suberates, sebacates, fumarates, maleates, dioates, benzoates, chlorobenzoates, methylbenzoates, dinitromenzoates, hydroxybenzoates, methoxybenzoates, phthalates, sulfonates, toluenesulfonates, xylenesulfonates, pheylacetates, phenylpropionates, phenylbutyrates, citrates, lactates, γ-hydroxybutyrates, glycollates, tartrates, methanesulfonates, propanesulfonates, mandelates, and other salts customarily used or otherwise U.S. FDA-approved.

Depleting includes reducing, decreasing, blocking, preventing, delaying, stopping, and/or downregulating the biologic activity or expression of a molecule or pathway of interest. By way of example, but not of limitation, depleting XIAP protein includes reducing detectable levels of XIAP, which may include degrading XIAP protein in a cell.

Anticancer therapeutic regimens trigger tumor cell death largely through the induction of apoptosis. Recent experiments demonstrated that treatment of prostate cancer cells with the zinc chelating agent N,N,N',N'-tetrakis(2-pyridylmethyl)-ethylenediamine (TPEN) induces selective and rapid depletion of the X-linked inhibitor of apoptosis protein (XIAP), a gatekeeper molecule that determines apoptosis resistance in tumor cells of various origins. Other studies have demonstrated that down-regulation of XIAP results in marked sensitization of cancer cells to drug-mediated apoptosis (Cheung H H et al. (2006) Clin. Cancer Res. 12:3238-42; Schimmer A D, et al. (2006) Cell Death Differ. 13:179-88; and Schimmer A D et al. (2004) Cancer Cell 5:25-35). It is believed that coupling delivery of zinc chelating compounds with that of a chemo- and/or immunotherapeutic agents may markedly increase the therapeutic index of a given agent.

The process whereby a normal prostate epithelial cell transforms into a cancerous cell involves the loss of the cell's ability to accumulate intracellular zinc. This loss of zinc accumulation is one of the most consistent and persistent characteristics of prostatic malignancy. Zinc-deficient cancer cells are more sensitive to zinc depletion compared with normal zinc-accumulating cells.

It has been observed in accordance with the invention that novel zinc chelating agents of Formula I and Formula II induce selective and rapid depletion of XIAP in prostate cancer cells at least as effectively as TPEN. In some cases, XIAP was completely or nearly completely depleted. In addition, it has been observed that these chelating agents, when combined with TNF-related apoptosis-inducing ligand (TRAIL), induced significant levels of apoptosis in TRAIL-resistant prostate cancer cells. The level of apoptosis with a combination of the chelating agent and TRAIL was 6-8 fold higher than the level of apoptosis observed from the chelator alone, and upwards of 16-fold higher than the level of apoptosis observed from TRAIL alone. Accordingly, the invention features zinc chelating agents of Formula I, Formula II, and Formula V, compositions comprising these agents, kits comprising these agents, and methods of using these agents for inducing cell death in cancer cells. The methods may be carried out in vivo, in vitro, or in situ.

A composition may comprise a zinc chelator of Formula I, or a pharmaceutically acceptable salt thereof, and a carrier. A composition may comprise a zinc chelator of Formula II, or a pharmaceutically acceptable salt thereof, and a carrier. A composition may comprise a zinc chelator of Formula V, or a pharmaceutically acceptable salt thereof, and a carrier. A carrier may comprise a pharmaceutically acceptable carrier. Pharmaceutically acceptable carriers include any that do not interfere (or substantially interfere) with the biological activity of the Formula I, Formula II, or Formula V compound, including zinc chelating activity, and preferably is not toxic to the subject to which it is administered. Pharmaceutically acceptable carriers include aqueous vehicles such as water, alcohol (e.g., ethanol or glycol), saline solutions, dextrose solutions, and balanced salt solutions, or a physiologically compatible buffer, such as Hanks's solution, Ringer's solution, or physiological saline buffer, as well as nonaqueous vehicles such as alcohols and oils, including plant or vegetable-derived oils such as olive oil, cottonseed oil, corn oil, canola oil, sesame oil, and other non-toxic oils. The carrier may contain formulatory agents, such as suspending, stabilizing and/or dispersing agents. The compositions may comprise one or more pharmaceutically acceptable excipients.

The compositions preferably comprise a therapeutically effective amount of the compound such as a compound having Formula I, Formula II, Formula V, or pharmaceutically acceptable salt of Formula I, Formula II, or Formula V. A therapeutically effective amount may comprise an amount effective to chelate zinc in a tumor cell, an amount effective to enhance sensitivity of a tumor cell to an apoptosis-inducing agent, an amount effective to induce apoptosis in an apoptosis-resistant tumor cell, or an amount effective to treat an apoptosis-resistant tumor cell in a subject in need thereof. The compositions may be prepared to provide from about 0.05 mg to about 1000 mg of the compound (Formula I, Formula II, or Formula V), or pharmaceutically acceptable salt thereof. The compositions may comprise from about 1 mg to about 200 mg of the compound, may comprise from about 10 mg to about 200 mg of the compound, may comprise from about 10 mg to about 100 mg of the compound, may comprise from about 50 mg to about 100 mg of the compound, may comprise from about 50 mg to about 250 mg of the compound, may comprise from about 50 mg to about 400 mg of the compound, may comprise from about 100 mg to about 200 mg of the compound, may comprise from about 100 mg to about 300 mg of the compound, may comprise about 200 mg to about 250 mg of the compound, may comprise about 225 mg to about 325 mg of the compound, may comprise about 300 mg to about 400 mg of the compound, may comprise about 400 mg to about 600 mg of the compound, may comprise about 500 mg to about 750 mg of the compound, may comprise about 500 mg to about 1000 mg of the compound, may comprise about 600 mg to about 700 mg of the compound, and, may comprise from about 750 mg to about 900 mg of the compound, or pharmaceutically acceptable salt thereof. The compositions may comprise from about 1 mg, about 50 mg, about 100 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1000 mg of the compound or pharmaceutically acceptable salt thereof, though the composition may comprise amounts lesser than about 1 mg or greater than about 1000 mg in some aspects. It is to be understood, however, that the concentration may vary depending on the cell type, tumor type, physical characteristics of the subject (species, age, height, weight, gender, among others).

The compositions may be formulated for administration to a subject in any suitable dosage form. The compositions may be formulated for oral, buccal, nasal, transdermal, parenteral, injectable, intravenous, subcutaneous, intramuscular, rectal, or vaginal administrations. The compositions may be formulated in a suitable controlled-release vehicle, with an adjuvant, or as a depot formulation.

Preparations for parenteral administration include sterile solutions ready for injection, sterile dry soluble products ready to be combined with a solvent just prior to use, including hypodermic tablets, sterile suspensions ready for injection, sterile dry insoluble products ready to be combined with a vehicle just prior to use and sterile emulsions.

Solid dosage forms include tablets, pills, powders, bulk powders, capsules, granules, and combinations thereof. Solid dosage forms may be prepared as compressed, chewable lozenges and tablets which may be enteric-coated, sugar coated or film-coated. Solid dosage forms may be hard or encased in soft gelatin, and granules and powders may be provided in non-effervescent or effervescent form. Solid dosage forms may be prepared for dissolution or suspension in a liquid or semi-liquid vehicle prior to administration.

Liquid dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions may be oil-in water or water-in-oil emulsions.

Pharmaceutically acceptable excipients utilized in solid dosage forms include coatings, binders, lubricants, diluents, disintegrating agents, coloring agents, flavoring agents, preservatives, sweeteners, and wetting agents. Enteric-coated tablets, due to their enteric-coating, resist the action of stomach acid and dissolve or disintegrate in the neutral or alkaline intestines. Other examples of coatings include sugar coatings and polymer coatings. Sweetening agents are especially useful in the formation of chewable tablets and lozenges. Pharmaceutically acceptable excipients used in liquid dosage forms includes solvents, suspending agents, dispersing agents, emulsifying agents, surfactants, emollients, coloring agents, flavoring agents, preservatives, and sweeteners.

Non-limiting examples of binders include glucose solution, *acacia* mucilage, gelatin solution, sucrose and starch paste. Non-limiting examples of lubricants include talc, starch, magnesium or calcium stearate, lycopodium and stearic acid. Non-limiting examples of diluents include lactose, sucrose, starch, kaolin, salt, mannitol and dicalcium phosphate. Non-limiting examples of disintegrating agents include corn starch, potato starch, bentonite, methylcellulose, agar and carboxymethylcellulose. Non-limiting examples of emulsifying agents include gelatin, *acacia*, tragacanth, bentonite, and surfactants such as polyoxyethylene sorbitan monooleate. Non-limiting examples of suspending agents include sodium carboxymethylcellulose, pectin, tragacanth, veegum and *acacia*.

Non-limiting examples of coloring agents include any of the approved certified water soluble FD and C dyes, mixtures thereof, and water insoluble FD and D dyes suspended on alumina hydrate. Non-limiting examples of sweetening agents include dextrose, sucrose, fructose, lactose, mannitol and artificial sweetening agents such as saccharin, aspartame, sucralose, acelsulfame potassium, and other artificial sweeteners. Non-limiting examples of flavoring agents include synthetic flavors and natural flavors extracted from plants such as fruits and mints, and synthetic blends of compounds which produce a pleasant sensation. Non-limiting examples of wetting agents include propylene glycol monostearate, sorbitan monooleate, diethylene glycol monolaurate and polyoxyethylene laural ether. Non-limiting examples of enteric-coatings include fatty acids, fats, waxes, shellac, ammoniated shellac and cellulose acetate phthalates. Non-limiting examples of film coatings include hydroxyethylcellulose, sodium carboxymethylcellulose, polyethylene glycol 4000 and cellulose acetate phthalate. Non-limiting examples of preservatives include glycerin, methyl and propylparaben, ethylparaben, butylparaben, isobutylparaben, isopropylparaben, benzylparaben, citrate, benzoic acid, sodium benzoate and alcohol.

Elixirs include clear, sweetened, hydroalcoholic preparations. Pharmaceutically acceptable carriers used in elixirs include solvents. Syrups include concentrated aqueous solutions of a sugar, for example, sucrose, and may contain a preservative. An emulsion is a two-phase system in which one liquid is dispersed throughout another liquid. Pharmaceutically acceptable carriers used in emulsions may include emulsifying agents and preservatives. Suspensions may use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substance used in effervescent granules, to be reconstituted into a liquid oral dosage form, include organic acids and a source of carbon dioxide. Sources of carbon dioxide include sodium bicarbonate and sodium carbonate. Coloring and flavoring agents may be used in all such dosage forms.

Additional excipients that may be included in any dosage forms include, but are not limited to antimicrobial agents, isotonic agents, buffers, antioxidants, local anesthetic agents, sequestering or chelating agents, analgesic agents, antiemetic agents, and other agents to enhance selected characteristics of the formulation.

Antimicrobial agents may be cidal or static, and may be antimicrobial, antifungal, antiparasitic, or antiviral. Non-limiting examples of commonly used antimicrobial agents include phenols or cresols, mercurials, benzyl alcohol, chlorobutanol, methyl and propyl p-hydroxybenzoic acid esters, thimerosal, benzalkonium chloride and benzethonium chloride. Acidic or basic pH may be used for antimicrobial effects in some aspects. Non-limiting examples of isotonic agents include sodium chloride and dextrose. Non-limiting examples of buffers include phosphate and citrate buffers.

The compositions may also be formulated in sustained release vehicles or depot preparations. For example, the compositions may be formulated with suitable polymeric or hydrophobic materials (for example, as an emulsion in an acceptable oil) or ion exchange resins, or as sparingly soluble derivatives, for example, as a sparingly soluble salt. Liposomes, micelles, and emulsions are well-known examples of such delivery vehicles.

The invention also features methods for depleting XIAP in a cell. In some aspects, the methods comprise contacting the cell with an amount of a compound having Formula I, or a pharmaceutically acceptable salt thereof, effective to deplete XIAP in the cell. In some aspects, the methods comprise contacting the cell with an amount of a compound having Formula II, or a pharmaceutically acceptable salt thereof, effective to deplete XIAP in the cell. In some aspects, the methods comprise contacting the cell with an amount of a compound having Formula V, or a pharmaceutically acceptable salt thereof, effective to deplete XIAP in the cell. Formula I or Formula II or Formula V may be comprised in a composition.

The cell is preferably a tumor cell. The tumor cell may be a tumor cell of the pancreas, a tumor cell of the head and neck, a tumor cell of the lung, a tumor cell of the kidney, a tumor cell of the breast, a tumor cell of the colon, a tumor cell of the ovary, a tumor cell of a lymph node, a tumor cell of the stomach, a tumor cell of the esophagus, a tumor cell of the skin, a tumor cell of the brain, a tumor cell of the oral cavity, a tumor cell of the pharynx, a tumor cell of the thyroid, a tumor of the adrenal gland, a leukemia cell, a sarcoma cell, a tumor cell of the testes, a tumor cell of the bladder, or a tumor cell of the prostate gland. Prostate gland tumor cells are highly preferred, including but not limited to castration-resistant prostate tumor cells. The cell may be in a cell culture. The cell may be present in or otherwise comprise a tumor tissue.

XIAP depletion may be measured according to the level of XIAP depletion in a cell of the same type that has not been contacted with Formula I, Formula II, or Formula V, or pharmaceutically acceptable salt thereof. In some aspects, XIAP depletion may be measured relative to the normal amount of XIAP in the cell, and what is normal may vary according to a healthy (non-cancerous) cell, or a tumor cell (including a tumor cell of a stage I, stage II, stage III, or stage IV tumor), and/or the particular cell type. Where a cell is a tumor cell, the normal amount of XIAP in the cell is not necessarily the amount of XIAP in a healthy, non-tumor cell. XIAP depletion may be measured according to any technique suitable in the art, and may be measured at the gene (e.g., mRNA) level, and/or the protein level. Without intending to be limited to any particular theory or mechanism of action, it is believed that zinc chelation induces degradation of the XIAP protein, acting post-translationally.

The amount of XIAP depletion may comprise depletion of about 20% to about 100% of the level of XIAP in the cell. The amount of XIAP depletion may comprise depletion of about 50% to about 99% of the level of XIAP in the cell. The amount of XIAP depletion may comprise depletion of about 50% to about 95% of the level of XIAP in the cell. The amount of XIAP depletion may comprise depletion of about 60% to about 80% of the level of XIAP in the cell. The amount of XIAP depletion may comprise depletion of about 70% to about 90% of the level of XIAP in the cell. The amount of XIAP depletion may comprise depletion of about 75% to about 99% of the level of XIAP in the cell. The amount of XIAP depletion may comprise depletion of about 80% to about 95% of the level of XIAP in the cell. The amount of XIAP depletion may comprise depletion of about 85% to about 99% of the level of XIAP in the cell. The amount of XIAP depletion may comprise depletion of about 85% to about 95% of the level of XIAP in the cell. The amount of XIAP depletion may comprise depletion of about 90% to about 99% of the level of XIAP in the cell. The amount of XIAP depletion may comprise depletion of about 90% to about 95% of the level of XIAP in the cell. The amount of XIAP depletion may comprise depletion of about 90% to about 100% of the level of XIAP in the cell. The amount of XIAP depletion may comprise depletion of about 95% to about 99% of the level of XIAP in the cell. The amount of XIAP depletion may comprise depletion of about 95% to about 100% of the level of XIAP in the cell. The amount of XIAP depletion may comprise about 50%, about 55%, about 60%, about 65%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% of the XIAP in the cell. XIAP may be substantially depleted. Greater than about 50% of XIAP may be depleted in the cell. Greater than about 60% of XIAP may be depleted in the cell. Greater than about 70% of XIAP may be depleted in the cell. Greater than about 75% of XIAP may be depleted in the cell. Greater than about 80% of XIAP may be depleted in the cell. Greater than about 85% of XIAP may be depleted in the cell. Greater than about 90% of XIAP may be depleted in the cell. Greater than about 91% of XIAP may be depleted in the cell. Greater than about 92% of XIAP may be depleted in the cell. Greater than about 93% of XIAP may be depleted in the cell. Greater than about 94% of XIAP may be depleted in the cell. Greater than about 95% of XIAP may be depleted in the cell. Greater than about 96% of XIAP may be depleted in the cell. Greater than about 97% of XIAP may be depleted in the cell. Greater than about 98% of XIAP may be depleted in the cell. Greater than about 99% of XIAP may be depleted in the cell.

In some aspects, the invention provides methods for enhancing the sensitivity of a tumor cell to an apoptosis-inducing agent. The methods generally comprise depleting XIAP in the cell and/or chelating zinc in the cell. Prostate gland tumor cells are highly preferred, including but not limited to castration-resistant prostate tumor cells. The cell may be in a cell culture. The cell may comprise a tumor tissue. The cell may be resistant or substantially resistant, as measured according to any suitable technique or standard, to the apoptosis-inducing agent. Thus, for example, the methods may sensitize a cell that is resistant to apoptosis (as normally induced by contact with an effective amount of the agent) caused by the agent, such that upon zinc chelation, the cell will undergo apoptosis when contacted with the agent, or will undergo apoptosis when contacted with lesser amounts of the agent, or will undergo apoptosis when contacted with amounts of the agent to which the cell is resistant.

XIAP is preferably depleted by chelating zinc in the cell. Zinc is preferably chelated by contacting the cell with an amount of a compound having Formula I, Formula II, or Formula V, or a pharmaceutically acceptable salt thereof, effective to chelate zinc in the cell. In some aspects, the methods comprise contacting the cell with an amount of a compound having Formula I, or a pharmaceutically acceptable salt thereof, effective to chelate zinc in the cell. In some aspects, the methods comprise contacting the cell with an amount of a compound having Formula II, or a pharmaceutically acceptable salt thereof, effective to chelate zinc in the cell. In some aspects, the methods comprise contacting the cell with an amount of a compound having Formula V, or a pharmaceutically acceptable salt thereof, effective to chelate zinc in the cell. Formula I or Formula II or Formula V may be comprised in a composition. The zinc is preferably zinc in ionic form. A preferred zinc ion is the zinc (II) ion.

The amount of zinc chelated is preferably an amount effective for sensitizing the cell to treatment with an apoptosis-inducing agent such that the cell will undergo apoptosis, or programmed cell death if contacted with an amount of the agent effective to induce apoptosis. The amount of zinc chelated may be an amount effective to deplete XIAP levels in the cell. The amount of XIAP may be an amount described or exemplified herein. It is believed that for those zinc chelators that possess a binding constant that affords 1:1 zinc chelation, equimolar concentration of chelator is required (e.g., for substantially all XIAP to be depleted, substantially all cellular zinc needs to be bound), and that for weaker zinc chelators, higher concentrations of zinc chelators may be necessary.

The methods are suitable for sensitizing the cell to any apoptosis-inducing agent to which the cell is resistant. In preferred aspects, the methods sensitize the cells to TRAIL, or an apoptosis-inducing analog, derivative, homolog, or variant of TRAIL, or any agent that agonizes the TRAIL receptor to induce apoptosis. Zinc chelation may sensitize a tumor cell to apoptosis in response to any agent that activates a cell death receptor, non-limiting examples of which include Fas/CD95, TNF-alpha, TRAIL (including Mapatumumab (HGS-ETR1), a human monoclonal antibody that induces cancer-cell death in a highly targeted way by activating the protein known as TRAIL receptor 1). XIAP depletion also sensitizes cancer cells to various chemotherapeutic agents, and thus may sensitize the cell to a chemotherapeutic agent (Schimmer A D et al. (2006) Cell Death Differ. 13:179-188).

The invention also features methods for inducing apoptosis in an apoptosis-resistant cell. In some aspects, the methods comprise chelating zinc in the cell and contacting the cell with an amount of an apoptosis-inducing agent effective to induce apoptosis in the cell. In some alternative aspects, the methods comprise depleting XIAP in the cell and contacting the cell with an amount of an apoptosis-inducing agent effective to induce apoptosis.

In some aspects of the methods, chelating zinc may comprise contacting the cell with an amount of a compound having Formula I, or a pharmaceutically acceptable salt thereof, effective to chelate zinc in the cell. In some aspects of the methods, chelating zinc may comprise contacting the cell with an amount of a compound having Formula II, or a pharmaceutically acceptable salt thereof, effective to chelate zinc in the cell. In some aspects of the methods, chelating zinc may comprise contacting the cell with an amount of a compound having Formula V, or a pharmaceutically acceptable salt thereof, effective to chelate zinc in the cell. Formula I or Formula II or Formula V may be comprised in a composition. The zinc is preferably zinc in ionic form. A preferred zinc ion is the zinc (II) ion. The amount of zinc chelation preferably is an amount sufficient to sensitize the cell to the induction of apoptosis upon contact with the apoptosis-inducing agent.

In some aspects of the methods, depleting XIAP may comprise contacting the cell with an amount of a compound having Formula I, or a pharmaceutically acceptable salt thereof, effective to deplete XIAP in the cell. In some aspects of the methods, depleting XIAP may comprise contacting the cell with an amount of a compound having Formula II, or a pharmaceutically acceptable salt thereof, effective to deplete XIAP in the cell. In some aspects of the methods, depleting XIAP may comprise contacting the cell with an amount of a compound having Formula V, or a pharmaceutically acceptable salt thereof, effective to deplete XIAP in the cell. Formula I or Formula II or Formula V may be comprised in a composition comprising a pharmaceutically acceptable carrier. The amount of XIAP depletion preferably is an amount sufficient to sensitize the cell to the induction of apoptosis upon contact with the apoptosis-inducing agent. The amount of XIAP depletion may be an amount described or exemplified herein.

The cell is preferably a tumor cell. The tumor cell may be a tumor cell of the pancreas, a tumor cell of the head and neck, a tumor cell of the lung, a tumor cell of the kidney, a tumor cell of the breast, a tumor cell of the colon, a tumor cell of the ovary, a tumor cell of a lymph node, a tumor cell of the stomach, a tumor cell of the esophagus, a tumor cell of the skin, a tumor cell of the brain, a tumor cell of the oral cavity, a tumor cell of the pharynx, a tumor cell of the thyroid, a tumor of the adrenal gland, a leukemia cell, a sarcoma cell, a tumor cell of the testes, a tumor cell of the bladder, or a tumor cell of the prostate gland. Prostate gland tumor cells are highly preferred, including but not limited to castration-resistant prostate tumor cells. The cell may be in a cell culture. The cell may comprise a tumor tissue.

The apoptosis inducing agent may be any agent whose apoptosis-inducing activity or capability is caused, facilitated, or enhanced by chelating zinc and/or depleting XIAP in the cell. The agent is preferably TRAIL, or an apoptosis-inducing analog, homolog, derivative, or variant of TRAIL, or any TRAIL receptor agonist that induces apoptosis in the cell. Zinc chelation may sensitize a tumor cell to apoptosis in response to any agent that activates a cell death receptor, non-limiting examples of which include Fas/CD95, TNF-alpha, TRAIL (including Mapatumumab (HGS-ETR1), a human monoclonal antibody that induces cancer-cell death in a highly targeted way by activating the protein known as TRAIL receptor 1). The agent may be in a composition comprising a pharmaceutically acceptable carrier In accordance with the methods, the cell may be resistant or substantially resistant to the apoptosis-inducing agent in the absence of zinc chelation and/or XIAP depletion. Thus, for example, upon zinc chelation and/or XIAP depletion the cell will undergo apoptosis when contacted with the agent, or will undergo apoptosis when contacted with lesser amounts of the agent, or will undergo apoptosis when contacted with amounts of the agent to which the cell is resistant (e.g., resistant when intracellular zinc is not chelated or when XIAP levels are not depleted).

The methods are a combination therapy, in which the cell is contacted with an agent to chelate zinc and/or to deplete XIAP, and contacted with an agent to induce apoptosis. The zinc chelating agent or XIAP-depleting agent may be contacted with the cell before the cell is contacted with the apoptosis-inducing agent, or substantially at the same time as the cell is contacted with the apoptosis-inducing agent, although in some aspects, the agent may be contacted with the cell after the cell is contacted with the apoptosis-inducing agent.

In one detailed aspect, the method comprises contacting the cell with an amount of a compound having Formula I, or pharmaceutically acceptable salt thereof, effective to chelate zinc in the cell, and contacting the cell with an amount of TRAIL effective to induce apoptosis in the cell. In one detailed aspect, the method comprises contacting the cell with an amount of a compound having Formula II, or pharmaceutically acceptable salt thereof, effective to chelate zinc in the cell, and contacting the cell with an amount of TRAIL effective to induce apoptosis in the cell. In one detailed aspect, the method comprises contacting the cell with an amount of a compound having Formula V, or pharmaceutically acceptable salt thereof, effective to chelate zinc in the cell, and contacting the cell with an amount of TRAIL effective to induce apoptosis in the cell. In one detailed aspect, the method comprises contacting the cell with an amount of a compound having Formula I, or pharmaceutically acceptable salt thereof, effective to deplete XIAP in the cell, and contacting the cell with an amount of TRAIL effective to induce apoptosis in the cell. In one detailed aspect, the method comprises contacting the cell with an amount of a compound having Formula II, or pharmaceutically acceptable salt thereof, effective to deplete XIAP in the cell, and contacting the cell with an amount of TRAIL effective to induce apoptosis in the cell. In one detailed aspect, the method comprises contacting the cell with an amount of a compound having Formula V, or pharmaceutically acceptable salt thereof, effective to deplete XIAP in the cell, and contacting the cell with an amount of TRAIL effective to induce apoptosis in the cell. The cell is preferably a prostate cancer cell. The prostate cancer cell may be a castration-resistant prostate cancer cell. The prostate cancer cell may be resistant to TRAIL.

The invention also features methods for treating apoptosis-resistant tumor in a subject in need thereof. In some aspects, the methods comprise administering to the subject an amount of a zinc chelating agent effective to chelate zinc in cells of the tumor, and administering to the subject an amount of an apoptosis-inducing agent effective to induce apoptosis in cells of the tumor in which zinc has been chelated by the zinc chelating agent. In some aspects, the methods comprise administering to the subject an amount of a XIAP depleting agent effective to deplete XIAP in cells of the tumor, and administering to the subject an amount of an apoptosis-inducing agent effective to induce apoptosis in cells of the tumor in which XIAP has been depleted by the XIAP depleting agent. Inducing apoptosis causes cells of the tumor to die, thereby treating the tumor.

The methods may comprise administering to the subject an amount of a compound having Formula I, or a pharmaceutically acceptable salt thereof, effective to chelate zinc in cells of the tumor (zinc chelating agent). The methods may comprise administering to the subject an amount of a compound having Formula I, or a pharmaceutically acceptable salt thereof, effective to deplete XIAP in cells of the tumor (XIAP depleting agent). The methods may comprise administering to the subject an amount of a compound having Formula II, or a pharmaceutically acceptable salt thereof, effective to chelate zinc in cells of the tumor (zinc chelating agent). The methods may comprise administering to the subject an amount of a compound having Formula II, or a pharmaceutically acceptable salt thereof, effective to deplete XIAP in cells of the tumor (XIAP depleting agent). The methods may comprise administering to the subject an amount of a compound having Formula V, or a pharmaceutically acceptable salt thereof, effective to chelate zinc in cells of the tumor (zinc chelating agent). The methods may comprise administering to the subject an amount of a compound having Formula V, or a pharmaceutically acceptable salt thereof, effective to deplete XIAP in cells of the tumor (XIAP depleting agent). Formula I or Formula II or Formula V may be comprised in a composition comprising a pharmaceutically acceptable carrier.

The methods may comprise administering to the subject an amount of TRAIL effective to induce apoptosis in cells of the tumor in which zinc has been chelated and/or in which XIAP has been deleted. The agent may comprise an apoptosis-inducing analog, homolog, derivative, or variant of TRAIL. The TRAIL may be in a composition comprising a pharmaceutically acceptable carrier. Zinc chelation may sensitize a tumor cell to apoptosis in response to any agent that activates a cell death receptor, non-limiting examples of which include Fas/CD95, TNF-alpha, TRAIL (including Mapatumumab (HGS-ETR1), a human monoclonal antibody that induces cancer-cell death in a highly targeted way by activating the protein known as TRAIL receptor 1), and such an agent may be in a composition comprising a pharmaceutically acceptable carrier.

In one detailed aspect, the method comprises administering to the subject an amount of a compound having Formula I, or pharmaceutically acceptable salt thereof, effective to chelate zinc in cells of the tumor, and administering to the subject an amount of TRAIL effective to induce apoptosis in cells of the tumor in which zinc has been chelated. In one detailed aspect, the method comprises administering to the subject an amount of a compound having Formula II, or pharmaceutically acceptable salt thereof, effective to chelate zinc in cells of the tumor, and administering to the subject an amount of TRAIL effective to induce apoptosis in cells of the tumor in which zinc has been chelated. In one detailed aspect, the method comprises administering to the subject an amount of a compound having Formula V, or pharmaceutically acceptable salt thereof, effective to chelate zinc in cells of the tumor, and administering to the subject an amount of TRAIL effective to induce apoptosis in cells of the tumor in which zinc has been chelated. In one detailed aspect, the method comprises administering to the subject an amount of a compound having Formula I, or pharmaceutically acceptable salt thereof, effective to deplete XIAP in cells of the tumor, and administering to the subject an amount of TRAIL effective to induce apoptosis in cells of the tumor in which XIAP has been deleted. In one detailed aspect, the method comprises administering to the subject an amount of a compound having Formula II, or pharmaceutically acceptable salt thereof, effective to deplete XIAP in cells of the tumor, and administering to the subject an amount of TRAIL effective to induce apoptosis in cells of the tumor in which XIAP has been deleted. In one detailed aspect, the method comprises administering to the subject an amount of a compound having Formula V, or pharmaceutically acceptable salt thereof, effective to deplete XIAP in cells of the tumor, and administering to the subject an amount of TRAIL effective to induce apoptosis in cells of the tumor in which XIAP has been deleted. The cell is preferably a prostate cancer cell. The prostate cancer cell may be a castration-resistant prostate cancer cell. The prostate cancer cell may be resistant to TRAIL.

Each agent (zinc chelating, XIAP depleting, and/or apoptosis inducing) may be administered to the subject according to any technique suitable in the art. Each agent may be administered directly to or at least in the proximity of the tumor of interest. Administration may be by way of the blood or other biological fluid. Each agent may be specifically targeted to the tumor in the subject, for example, by using carriers, liposomes, antibodies, and/or magnets. Any suitable route or technique to administer the agent may be used, and may vary, for example, according to the needs of the investigator or according to the characteristics of the agent itself.

The apoptosis-resistant tumor preferably is resistant to the apoptosis-inducing agent, such that chelating zinc and/or depleting XIAP sensitizes the tumor to apoptosis from the apoptosis-inducing agent. The tumor may be any tumor in which zinc accumulation (especially the loss of zinc accumulation), zinc depletion, and/or the level of XIAP is/are a factor in apoptosis resistance. A tumor of the prostate gland, including a castration-resistant tumor, is a preferred target.

The invention also features kits. The kits may be used, for example, to carry out any of the methods described or exemplified herein. In some aspects, a kit comprises a zinc chelating agent having Formula I, or a pharmaceutically acceptable salt thereof, and may further comprise an apoptosis inducing agent, preferably TRAIL, and instructions for using the zinc chelating agent and, if present, the apoptosis inducing agent, in any of the methods described or exemplified herein. For example, the instructions may be for using the zinc chelating agent and, if present, the apoptosis inducing agent in a method for chelating zinc in a tumor cell. The instructions may be for using the zinc chelating agent and, if present, the apoptosis inducing agent in a method for depleting XIAP in a tumor cell. The instructions may be for using the zinc chelating agent and, if present, the apoptosis inducing agent in a method sensitizing a tumor cell to an apoptosis-inducing agent, including a tumor cell that is resistant to the agent. The instructions may be for using the zinc chelating agent and, if present, the apoptosis inducing agent in a method for treating a tumor of the prostate gland in a subject in need thereof.

In some aspects, a kit comprises a zinc chelating agent having Formula II, or a pharmaceutically acceptable salt thereof, and may further comprise an apoptosis inducing agent, preferably TRAIL, and instructions for using the zinc chelating agent and, if present, the apoptosis inducing agent, in any of the methods described or exemplified herein. For example, the instructions may be for using the zinc chelating agent and, if present, the apoptosis inducing agent in a method for chelating zinc in a tumor cell. The instructions may be for using the zinc chelating agent and, if present, the apoptosis inducing agent in a method for depleting XIAP in a tumor cell. The instructions may be for using the zinc chelating agent and, if present, the apoptosis inducing agent in a method sensitizing a tumor cell to an apoptosis-inducing agent, including a tumor cell that is resistant to the agent. The instructions may be for using the zinc chelating agent and, if present, the apoptosis inducing agent in a method for treating a tumor of the prostate gland in a subject in need thereof.

In some aspects, a kit comprises a zinc chelating agent having Formula V, or a pharmaceutically acceptable salt thereof, and may further comprise an apoptosis inducing agent, preferably TRAIL, and instructions for using the zinc chelating agent and, if present, the apoptosis inducing agent, in any of the methods described or exemplified herein. For example, the instructions may be for using the zinc chelating agent and, if present, the apoptosis inducing agent in a method for chelating zinc in a tumor cell. The instructions may be for using the zinc chelating agent and, if present, the apoptosis inducing agent in a method for depleting XIAP in a tumor cell. The instructions may be for using the zinc chelating agent and, if present, the apoptosis inducing agent in a method sensitizing a tumor cell to an apoptosis-inducing agent, including a tumor cell that is resistant to the agent. The instructions may be for using the zinc chelating agent and, if present, the apoptosis inducing agent in a method for treating a tumor of the prostate gland in a subject in need thereof.

The compounds described and exemplified herein (e.g., Formula I, Formula II, Formula V, and pharmaceutically acceptable salts thereof), may be for use as a medicament. Formulations of the compounds described and exemplified herein (e.g., Formula I, Formula II, Formula V, and pharmaceutically acceptable salts thereof together with a pharmaceutically acceptable carrier), may be for use as a medicament. The compounds (e.g., Formula I, Formula II, Formula V, and pharmaceutically acceptable salts thereof) and formulations (e.g., Formula I, Formula II, Formula V, and pharmaceutically acceptable salts thereof together with a pharmaceutically acceptable carrier) may be for use in the treatment of a tumor of the prostate gland. The compounds (e.g., Formula I, Formula II, Formula V, and pharmaceutically acceptable salts thereof) and formulations (e.g., Formula I, Formula II, Formula V, and pharmaceutically acceptable salts thereof together with a pharmaceutically acceptable carrier) may be for use in the treatment of an apoptosis-resistant tumor of the prostate gland. The compounds (e.g., Formula I, Formula II, Formula V, and pharmaceutically acceptable salts thereof) and formulations (e.g., Formula I, Formula II, Formula V, and pharmaceutically acceptable salts thereof together with a pharmaceutically acceptable carrier) may be for use in the treatment of a castration-resistant tumor of the prostate gland.

The compounds (e.g., Formula I, Formula II, Formula V, and pharmaceutically acceptable salts thereof) and formulations (e.g., Formula I, Formula II, Formula V, and pharmaceutically acceptable salts thereof together with a pharmaceutically acceptable carrier), in combination with an agent that induces apoptosis, such as TRAIL or a TRAIL receptor agonist that induces apoptosis, may be for use in the treatment of a tumor of the prostate gland. The compounds (e.g., Formula I, Formula II, Formula V, and pharmaceutically acceptable salts thereof) and formulations (e.g., Formula I, Formula II, Formula V, and pharmaceutically acceptable salts thereof together with a pharmaceutically acceptable carrier), in combination with an agent that induces apoptosis, such as TRAIL or a TRAIL receptor agonist that induces apoptosis, may be for use in the treatment of an apoptosis-resistant tumor of the prostate gland. The compounds (e.g., Formula I, Formula II, Formula V, and pharmaceutically acceptable salts thereof), in combination with an agent that induces apoptosis, such as TRAIL or a TRAIL receptor agonist that induces apoptosis, and formulations (e.g., Formula I, Formula II, Formula V, and pharmaceutically acceptable salts thereof together with a pharmaceutically acceptable carrier) may be for use in the treatment of a castration-resistant tumor of the prostate gland.

The invention also features methods for screening compounds for capability of depleting XIAP in a cell. The methods comprise contacting a zinc deficient cell with a test compound, and measuring the level of XIAP in the cells in the presence of the test compound relative to the level of XIAP in the cells in the absence of the test compound, wherein depletion of XIAP in the presence of the test compound indicates that the test compound is capable of depleting XIAP in the cell. The cell may be a prostate cancer cell, including a castration-resistant prostate cancer cell. The cell may be comprised in a cell culture.

The test compound is preferably a known or suspected zinc chelating agent. A test compound may be any purified molecule, substantially purified molecule, molecules that are one or more components of a mixture of compounds, or a mixture of a compound with any other material that can be analyzed using the methods described herein (e.g., a composition). Test compounds can be organic or inorganic chemicals, or biomolecules, and all fragments, analogs, homologs, conjugates, and derivatives thereof. Biomolecules include proteins, polypeptides, nucleic acids, lipids, monosaccharides, polysaccharides, and all fragments, analogs, homologs, conjugates, and derivatives thereof. Test compounds can be of natural or synthetic origin, and can be isolated or purified from their naturally occurring sources, or can be synthesized de novo. Test compounds can be defined in terms of structure or composition, or can be undefined. Test compounds can be an isolated product of unknown structure, a mixture of several known products, or an undefined composition comprising one or more compounds. Non-limiting examples of undefined compositions include cell and tissue extracts, growth medium in which cells have been cultured, and fermentation broths. The test compound can be contacted with the cell according to any means suitable in the art, and for any suitable period of time. The test compound can be assessed at multiple concentrations.

The screening method may further comprise contacting a second cell with the test compound and an apoptosis-inducing agent, for example, TRAIL, and determining the level of apoptosis in the cell in the presence of the test compound relative to the level of apoptosis in the cell in the absence of the test compound, wherein any increase, preferably a statistically significant increase, in apoptosis indicates that the test compound enhances the sensitivity of the cell to apoptosis induced by the apoptosis-inducing agent. The second cell may be resistant to the apoptosis-inducing agent. The second cell may be a zinc-deficient cell. The second cell may be a prostate cancer cell, including a castration-resistant prostate cancer cell. The second cell may be comprised in a cell culture.

The invention also features method for synthesizing a zinc chelating pro-drug. The zinc chelating pro-drug will lack the ability to chelate zinc until converted into active (drug) form. Conversion into active form may be by treatment of the pro-drug with a chemical or biomolecule that allows the drug to bind to zinc. For example, it is preferred that the pro-drug comprises moieties that are cleaved by esterases inside of a cell, whereupon the esterase-mediated cleavage activates the pro-drug into drug form.

The synthesizing method may comprise protecting zinc-binding moieties on a zinc chelating agent with a benzyl protecting group to form a benzyl-protected zinc chelating agent, and covalently coupling the benzyl-protected zinc chelating agent to a second benzyl-protected chelating with an amine-containing linking agent. The covalent coupling may comprise covalently bonding a carboxyl group on the zinc chelating agent to an amine group on the linking agent, thereby forming a carbodiimide (EDC). The covalent coupling may comprise forming a NHS ester bond between the zinc chelating agent and the linking agent. Suitable linking agents are shown in FIG. 6B.

The following examples are provided to describe the invention in greater detail. They are intended to illustrate, not to limit, the invention.

EXAMPLE 1

Preliminary Results

It has been demonstrated that zinc-specific chelator N,N, N',N'-tetrakis(2-pyridylmethyl)-ethylenediamine (TPEN) rapidly depletes XIAP in human prostate cancer cells. Makhov P et al. (2008) Cell Death Differ. 15:1745-51. TPEN exhibits specificity for malignant but not for benign cells. It is believed that the molecular mechanism for this specificity stems from blunted regulation of zinc uptake transporters in malignant cells compared with normal prostate epithelial cells. For instance, expression of zinc uptake transporters is significantly increased in benign tissues during low-zinc conditions, resulting in compensatory zinc uptake. In contrast, the expression of zinc uptake transporters is virtually undetectable in malignant prostate cells.

The inhibition of XIAP expression is selective, as TPEN has no effect on the expression levels of other zinc-containing members of IAP family, i.e., cIAP1, cIAP2 and surviving. As well, the XIAP mRNA level is not reduced in TPEN-treated cells. Therefore, zinc chelation by TPEN induces depletion of XIAP specifically at the protein level. TPEN treatment also produces a rapid decrease of XIAP protein levels in a xenograft animal model of human prostate cancer. The action of immunotherapeutic agents such as TRAIL Receptor-1 antibody (HGS-ETR1, mapatumumab) (Human Genome Sciences) and docetaxel are markedly potentiated by TPEN. Importantly, the sensitization to therapeutic agents is specific to malignant but not to benign cells. This cytotoxic specificity for malignant cells is consistent with experiments showing that XIAP is preferentially degraded in malignant but not in benign cells upon zinc chelation and stems from blunted regulation of zinc uptake transporters upon carcinogenesis.

Figure 2:
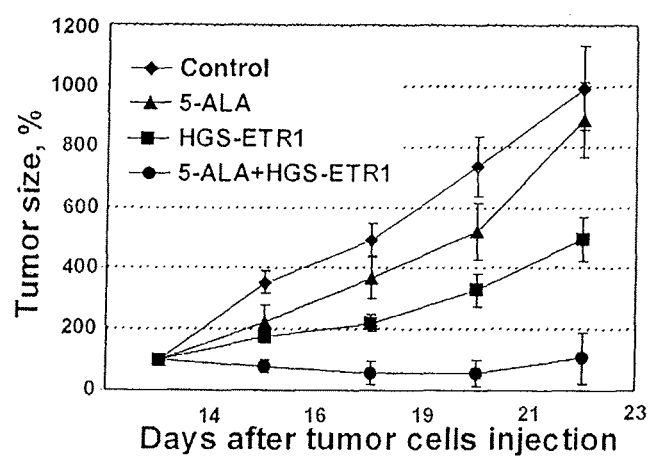
FIG. 2 shows that treatment with 5-Ala augments HGS-ETR1 the antitumor effect in an ectopic mouse model of prostate cancer. PC-3 tumors were established in male C.B17/Icr-scid mice. When tumor volumes reach approximately 200 mm³, the animals were grouped (n=5 for each group) and treated with saline (control), an ip injection of 5-Ala (10 mg/mouse, daily) and/or an iv injection of HGS-ETR1 (0.25 mg/mouse once a week).

To examine whether zinc-binding agents structurally distinct from TPEN are also capable of decreasing XIAP levels, cells were treated with either protoporphyrin IX (PPIX), a naturally occurring chelating molecule or its precursor 5-aminolevulinic acid (5-Ala). As demonstrated in FIG. 1, both agents significantly reduced XIAP expression in PC-3 cells. Importantly, combined 5-ALA and HGS-ETR1 treatment completely arrested tumor growth in xenograft animal model (FIG. 2).

EXAMPLE 2

Heterocyclic Zinc Chelators Materials and Methods

Synthesis of Heterocyclic Zn Chelators. The entire library of zinc chelators was supplied by the Department of Chemistry and Biochemistry from the University of California, San Diego.

Cell Lines and Culture Conditions. A PC-3 castration-resistant prostate cancer cell line was obtained from the American Type and Culture Collection (Rockville, Md.). PC-3 cells were maintained in complete cell culture medium (RPMI 1640 medium (Bio-Whittaker, Walkersville, Md.) supplemented with 10% FCS (Hyclone, Logan, Utah), gentamicin (50 mg/L), sodium pyruvate (1 mM) and non-essential amino acids (0.1 mM)).

Analysis of XIAP Depletion in PC-3 Cell Line Following Administration of Heterocyclic Zn Chelators. PC-3 cells were cultured under three distinct conditions; medium alone, with administration of TPEN (8 µM) as a positive control for 2 hours, and with administration of an individual Zn chelators (MR) (50 µM) for 4 hours.

Western blot analysis was performed to assess for level of XIAP depletion. Whole cell lysates were prepared as described previously (Kolenko V et al. (1999) J. Immunol. 163: 590-8). Protein concentrations were measured with BCA protein assay reagents (Pierce, Rockford, Ill.). Equivalent amounts of proteins (20 µg) were mixed with an equal volume of 2× Laemmli sample buffer, boiled and resolved by electrophoresis in 10% sodium dodecyl sulfate-polyacrylamide gels (SDS-PAGE). The proteins were transferred from the gel to a nitrocellulose membrane using an electroblotting apparatus (Bio-Rad) (15 V, 3 mA/cm2 for 24 minutes).

Membranes were then incubated in a blocking solution containing 5% nonfat dry milk overnight to inhibit nonspecific binding. The membranes were then incubated with specific antibody (1-3 µg/ml) for 2 hours. After washing in TRIS/ 0.1% Tween 20 for 30 minutes, membranes were incubated for another 30 minutes with horseradish peroxidase-conjugated secondary antibody. The membranes were then washed and developed with enhanced chemiluminescence (ECL Western Blotting Kit, Amersham, Arlington Heights, Ill.).

Animal Studies. Two 6 week-old male C.B17/Icr-scid mice were injected intravenously with 100 µl of MR13 chelator at final concentration of 15 mM. Intravenous administration of MR13 was well tolerated by both animals.

EXAMPLE 3

XIAP Depletion by New Zinc Chelating Agents

In pursuit of identifying more effective and biologically flexible zinc chelators, a versatile platform for the preparation of high-affinity zinc chelators and prochelators has been developed. The platform is based on bidentate ligands such as hydroxypyrones, hydroxypyrothiones, hydroxypyridinones (HOPOs), and hydroxypyridinethiones (HOPTOs), which are effective chelators of the zinc(II) ion. By taking advantage of the well-established coordination chemistry of these ligands with the zinc(II) ion, a series of zinc(II) sequestering agents has been developed.

Figures 3, 4:
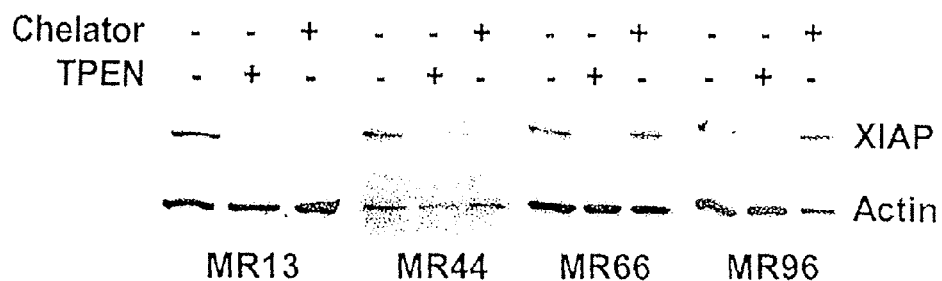
FIG. 3 shows a Western blot measuring the effect of various zinc chelating agents on the expression of XIAP; Parallel cell cultures were treated with TPEN as a positive control for zinc chelation. Beta-actin was screened as a negative control.
FIG. 4 shows a comparison of select chelating agents of against TPEN in the depletion of cellular levels of XIAP in castration-resistant prostate cancer cells.

The ability of novel heterocyclic zinc chelating agents to deplete cellular levels of XIAP in castration-resistant prostate cancer cells was assessed. One hundred and twenty candidate zinc chelating agents were tested in the screen. Some of these heterocyclic zinc chelators induced complete depletion of XIAP protein in PC-3 cells as demonstrated in FIG. 3. Actin was used to demonstrate equal protein loading. TPEN was used as a positive control. Notably, XIAP depletion was a reliable marker of ability to promote TRAIL-mediated apoptosis in prostate cancer cells as judged by the DNA fragmentation assay. As demonstrated in FIG. 4, MR13 (Formula I) and MR44 (Formula II) agents completely depleted XIAP and promoted TRAIL-mediated cell death in PC-3 cells. Meanwhile, agents such as MR66 (Formula III) and MR96 (Formula IV), failed to induce XIAP depletion and thus did not succeeded in producing an apoptotic response.

The invention is not limited to the embodiments described and exemplified above, but is capable of variation and modification within the scope of the appended claims.

We claim:

1. A method for inducing apoptosis in an apoptosis-resistant cell, comprising contacting an apoptosis-resistant cell with a compound selected from the group consisting of Formula I,

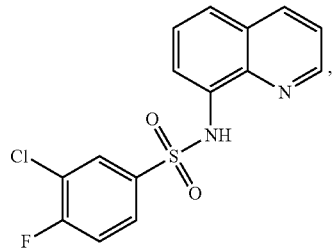

Formula II,

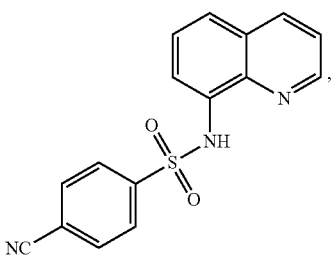

Formula V,

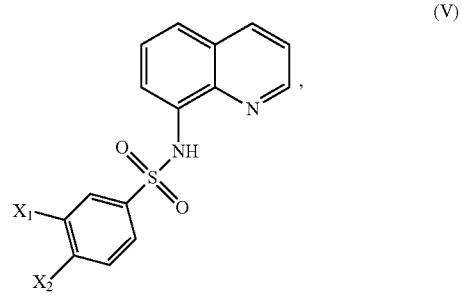

wherein X1 is H, Cl, or F and X2 is CN or F, and a pharmaceutically acceptable salt thereof, in an amount of effective to deplete X-linked inhibitor of apoptosis protein (XIAP) in the cell, and contacting the cell with an amount of an apoptosis-inducing agent effective to induce apoptosis in the cell.

2. The method of claim 1, wherein the compound is Formula I,

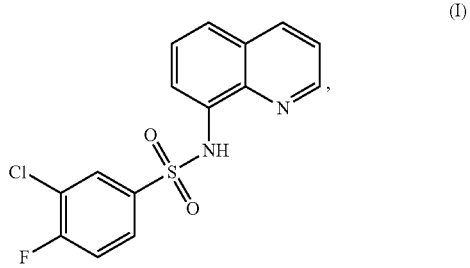 [SMILES: O=S(=O)(Nc1cccc2cccnc12)c1ccc(F)c(Cl)c1]

or a pharmaceutically acceptable salt thereof.

3. The method of claim 1, wherein the compound is Formula II,

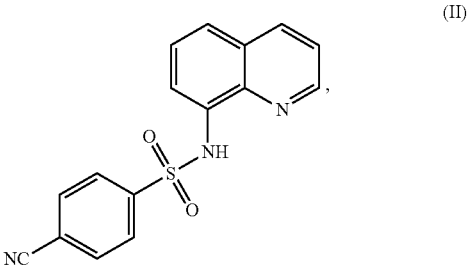 [SMILES: N#Cc1ccc(S(=O)(=O)Nc2cccc3cccnc23)cc1]

or a pharmaceutically acceptable salt thereof.

4. The method of claim 1, wherein the compound is Formula V,

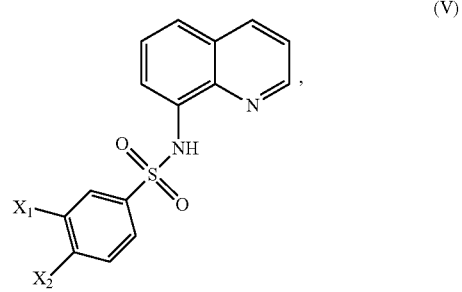

wherein X1 is H, Cl, or F and X2 is CN or F, or a pharmaceutically acceptable salt thereof.

5. The method of claim 1, wherein the apoptosis-inducing agent is TNF-related apoptosis-inducing ligand (TRAIL).

6. The method of claim 1, wherein the cell is a tumor cell.

7. The method of claim 6, wherein the tumor cell is a prostate tumor cell.

8. The method of claim 7, wherein the prostate tumor cell is a castration resistant prostate tumor cell.

9. The method of claim 1, wherein the compound substantially depletes XIAP in the cell.

10. A method for treating a tumor, comprising administering to a subject in need thereof a compound selected from the group consisting of Formula I,

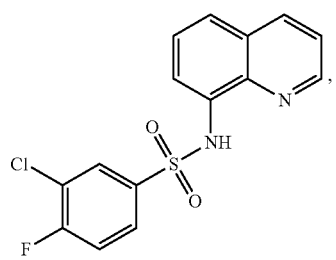

Formula II,

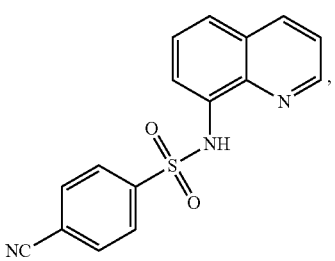

Formula V,

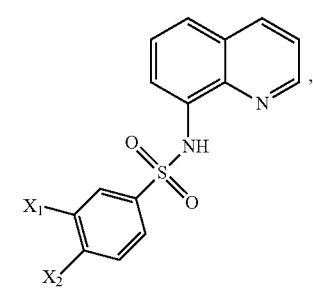

wherein X1 is H, Cl, or F and X2 is CN or F, and a pharmaceutically acceptable salt thereof, in an amount of effective to deplete X-linked inhibitor of apoptosis protein (XIAP) XIAP in cells of the tumor, and administering to the subject an apoptosis-inducing agent in an amount of effective to induce apoptosis in cells of the tumor in which XIAP has been depleted, thereby treating the tumor.

11. The method of claim 10, wherein the compound is Formula I,

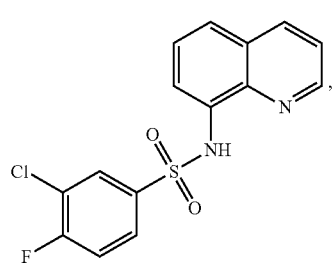

or a pharmaceutically acceptable salt thereof.

12. The method of claim 10, wherein the compound is Formula II,

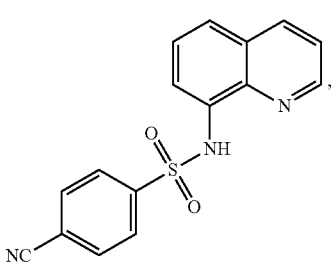

or a pharmaceutically acceptable salt thereof.

13. The method of claim 10, wherein the compound is Formula V,

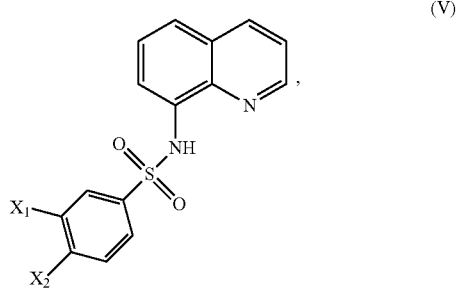

wherein X1 is H, Cl, or F and X2 is CN or F, or a pharmaceutically acceptable salt thereof.

14. The method of claim 10, wherein the apoptosis-inducing agent is TNF-related apoptosis-inducing ligand (TRAIL).

15. The method of claim 10, wherein the tumor is an apoptosis-resistant tumor.

16. The method of claim 10, wherein the tumor is a tumor of the prostate gland.

17. The method of claim 16, wherein the tumor of the prostate gland is a castration resistant tumor of the prostate gland.

18. The method of claim 10, wherein the compound substantially depletes XIAP in cells of the tumor.

* * * * *